United States Patent [19]

Frazier

[11] 4,160,322
[45] Jul. 10, 1979

[54] METHOD OF CONSTRUCTING AN ORTHODONTIC APPLIANCE

[76] Inventor: Paul D. Frazier, 6709 Old Stage Rd., Rockville, Md. 20852

[21] Appl. No.: 755,439

[22] Filed: Dec. 29, 1976

[51] Int. Cl.² ............................................. A61C 13/22
[52] U.S. Cl. .................................................... 32/14 C
[58] Field of Search ............................. 32/14 A, 14 B

[56] References Cited

U.S. PATENT DOCUMENTS

| | | | |
|---|---|---|---|
| 3,738,005 | 6/1973 | Cohen | 32/14 B |
| 3,949,478 | 4/1976 | Schinhammer | 32/14 B |
| 4,014,096 | 3/1977 | Dellinger | 32/14 A |

Primary Examiner—Robert Peshock
Attorney, Agent, or Firm—Haight & Huard

[57] ABSTRACT

A method of constructing an orthodontic appliance to be placed in a patient's mouth so as to effect desired tooth repositioning which includes the steps of initially making an impression of the patient's malocclusion and repositioning the teeth of the model so as to form an ideal model. A template is fabricated in accordance with the ideal model to properly position orthodontic brackets upon the ideal model so as to, in effect, ideally position the brackets relative to the teeth of the ideal model as well as with respect to each other. The brackets are then transferred from the ideal model to the patient's teeth with the aid of a transfer registration mold. The template is also used to guide fabrication of ideal arch wires which are to be selectively secured to the brackets at various stages of orthodontic treatment. A resilient finisher, also constructed in accordance with the ideal model, is adapted to be fixedly secured to the brackets disposed upon the teeth of the patient in order to accomplish finishing tooth movements.

6 Claims, No Drawings

METHOD OF CONSTRUCTING AN ORTHODONTIC APPLIANCE

BACKGROUND OF THE INVENTION

In the field of orthodontics, recent developments have led to direct bonding of brackets without bands to the buccal or labial surfaces of individual teeth. This is usually accomplished by one of two methods. The first involves direct positioning of the brackets onto the teeth, in the mouth, by the orthodontist. The second method involves attachment to a model of the malocclusion and subsequent use of a registration to transfer brackets to the mouth. Both techniques thus involve freehand means of positioning the brackets.

The brackets used in direct bonding are of several types and designs. They may be standard metal brackets attached to variously designed perforated metal bases. They may be plastic brackets with standard curved or flat bases for anterior or posterior placement. Also, they may be machined or cast metal brackets of a special design to compensate for tip, torque and tooth thickness.

Typically, only special brackets are designed to take into account the average size, shape and contour of the middle one-third of each individual tooth crown. Appliances constructed with these brackets require up to twenty-eight different individual brackets per patient, each with specific compound mesiodistal and occlusogingival base contours with pretorqued and preangulated slots. In addition to other inconveniences and inadequacies, large bracket inventories are required in order to accommodate right and left sides, upper and lower teeth and extraction and nonextraction treatment requirements.

The above described special brackets attempt to eliminate the need for torquing, tipping and in-out bends in the arch wire. These appliances reduce the need for wire manipulation compared to conventional appliances; however, they do not eliminate the need to adjust arch wires for arch size and arch form or to compensate for shortcomings in appliance design and placement. There are several reasons for these shortcomings. First, the design of individual bracket bases and torque and angulation of the slots are determined from mean values derived from measurements of a finite number of teeth and consequently cannot totally compensate for the vast variation in size and form of human teeth, including malformed teeth. Second, the special brackets are either positioned on the model for transfer to the mouth or placed directly in the mouth by handheld methods. Third, the appliance as constructed, either directly in the mouth or on a model of the malocclusion, provides no benefits with respect to arch size or arch form.

Inaccuracies of the current handheld means of positioning conventional and special brackets come into play in both direct and indirect placement methods. While the orthodontist may use a mechanical positioning device, errors cannot be eliminated since these devices are only empirically adjusted and are handheld. They thus serve only as a guide rather than as a precision positioning device. Furthermore, since the bracket base design and slot tip and torque are fixed, slight bracket malposition or tooth form variation results in cumulative positioning errors. The goal of eliminating arch wire manipulation is not obtained.

Techniques of appliance construction using models have been described. In one such technique, described in U.S. Pat. No. 3,842,503, brackets are attached to the teeth of a patient, an impression of the teeth with the brackets thereon is obtained and each tooth of the model containing an imprint of the bracket is then ideally positioned. Arch wires are then formed in relationship to the bracket imprints as determined by tooth position of the ideal model. These arch wires are then affixed to the brackets in the mouth. Such a technique may also involve inserting replicas of the brackets into the spaces in the impression left by the brackets which are attached in the mouth prior to forming a cast of each tooth in the impressions. The replicated teeth containing bracket replicas are then separated and formed into an ideal model and arch wires are formed to the model as described before.

A variation of this method involves brackets constructed on or affixed to the lingual surfaces of teeth. The method of the basic technique and its variations thus provide an indirect method of constructing arch wires. However, no attempt is made in this technique to ideally establish tip, torque or in-out positioning of the brackets themselves. Compensations for bracket errors in position are made in the arch wires on the model; this method thus makes arch wire bending more accurate and easier to accomplish by making it a laboratory procedure, rather than a clinical procedure. The need for tedious wire manipulations is thus not eliminated but merely transferred from the clinic to the laboratory.

Both methods described above involve nonprecision positioning of orthodontic brackets. Inaccuracies in placing appliances thus consistently necessitate arch wire manipulation to compensate for bracket position. The significance of this can be appreciated when it is understood that many arch wires are needed during the course of treatment of each dental arch and each malpositioned bracket requires compensating adjustment each time a new arch wire is constructed. Furthermore, since each tooth must be controlled in three planes of space, the edgewise arch wire frequently requires multiple separate adjustments such as for tip, torque, in-out, artistic and compensating bends.

OBJECTS OF THE INVENTION

Accordingly, it is an object of this invention to provide a precision method for positioning direct bonded orthodontic brackets onto teeth.

Another object of this invention is to provide a unique method of orienting orthodontic brackets to teeth and to each other utilizing a template system.

A further object of this invention is to provide a method of placing direct bonded brackets on teeth with all tip, torque and tooth thickness considerations compensated for.

Another object of this invention is to provide transfer registration techniques for carrying brackets to the mouth once they have been ideally positioned on an ideal model.

An additional object of this invention is to simplify arch wire construction, in advance if desirable, and to eliminate the need for either laboratory or clinical manipulation of arch wires to accomplish correct arch size and arch form, or to compensate for deficiencies in bracket design or bracket placement errors.

Another object of this invention is to provide an improved method for anchoring a resilient finishing appliance to facilitate more rapid and accurate case finishing.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing a method for constructing an orthodontic applicance to be placed in a patient's mouth so as to effect desired tooth repositioning, comprising the steps of:

making a model of the patient's malocclusion;

repositioning the teeth of said malocclusion with respect to each other and the opposing arch so as to form an ideal model;

providing a template which conforms to the arch size and form of said ideal model, and moving said template into juxtaposition relative to said ideal model;

fixing orthodontic brackets to the teeth of said ideal model in accordance with the positional characteristics of said template whereby each bracket will be ideally positioned upon each tooth of said model;

removing said template from the vicinity of said model; and transferring said brackets from said ideal model and affixing them to the teeth of said patient.

DETAILED DESCRIPTION OF THE INVENTION

In accordance with these considerations, the method, to be described hereinbelow, of constructing an orthodontic appliance eliminates the disadvantages inherent in prior art methods of banding and bonding standard or special brackets to the teeth. The invention also has major advantages over the other special methods of appliance construction described above.

The present invention totally eliminates freehand positioning of brackets onto the teeth, whether done directly or by the use of a model. The method can be used for positioning any bracket designed to be bonded, and eliminates the need to rely upon a special bracket with a built-in or inherent average base/torque/angulation/tooth relationship, although the benefits of these special brackets are enhanced when used in conjunction with the method of the present invention.

In accordance with the present invention, a template is utilized in conjunction with ideally positioned teeth upon a model. The bracket positions are maintained by means of the template, thereby allowing the bonding material to secure the final ideal positions of the brackets relative to the teeth. Once the brackets-teeth positions are established, a modified registration technique for indirect cementation facilitates transfer of the brackets to the same ideal teeth position in the mouth.

Several advantages of this technique are apparent. First, it results in unequivocal, ideal and precise bracket placements with all tip, torque and tooth thickness considerations compensated for individually upon a tooth-by-tooth basis for each arch. Thus, both laboratory and clinical manipulations of treatment wires for torque, tip, in-out bends and bracket malpositions are completely eliminated. Second, in accordance with this method, ideal arch size and arch form are determined, as a result of making the ideal model, prior to the commencement of treatment and thus all arch wires to be used throughout the course of treatment may be conveniently and accurately constructed in advance. Third, the placement procedure and the method, in general, provides a means for constructing appliances for mixed dentition cases since erupting teeth can be added to the case. Fourth, the brackets, which are ideally placed upon the teeth by this technique, may be used as locking devices for an elastic or rubber finisher. Fifth, the present invention reduces the need for practitioners to maintain large inventories of brackets for appliance construction. Sixth, the present invention provides easier, less time consuming and less expensive treatment of malocclusions by means of delegatng more procedures to auxiliary personnel and by reducing the chair time required for each case.

The first step of the present invention requires the preparation of an accurate impression of the patient's malocclusion, which may be obtained by standard dental and orthodontic techniques. It should be noted at this point that no brackets have been placed upon the patient's teeth and that the impression is accordingly of the teeth and jaws only. The individual teeth of the impression are then separated and repositioned into a configuration or model which is ideal for that particular patient's arch or set of arches. An impression of both arches is usually taken in order to obtain the correct orthodontic solution to a particular malocclusion; however, the present method can also be used when only one arch requires treatment. The ideal model so constructed becomes a master model which may be used directly or alternatively a duplicate master model may be constructed using standard orthodontic techniques. An individual template is then constructed to conform to the ideal model arch size and form, thereby allowing the orthodontic practitioner to ideally position all types of edgewise brackets which require positioning in accordance therewith. The template is placed in juxtaposition to the ideal model and the brackets are secured to the teeth of the ideal model so as to establish a base means while being held in an ideal position by means of the template. The template, having determined the optimum positioning of the brackets, is then removed, leaving the brackets upon the cast.

This procedure defines in every respect the correct overall positioning of the components of the bracket base thus formed, particularly the ideal relationship of each slot with respect to each individual tooth, adjacent bracket slots and the template. The template may subsequently be used as a pattern for constructing arch wires, either prior to or during treatment of the case; the arch wires are selectively secured to the bracket at various stages of treatment for orthodontically repositioning teeth.

The bracket base and bracket slot-to-tooth relationships, established upon the ideal model by means of the template just described, are preserved by means of a transfer registration mold. The initial steps of constructing the transfer registration mold encompass standard procedures and can be accomplished, for example, by vacuum forming a heat moldable material over the teeth and brackets. The transfer registeration mold thus obtained is removed from the model along with the brackets and the ideally formed base is defined thereby. The method of this invention thus differs at this point from prior art uses of such registration structures. In accordance with prior art methods, the brackets are bonded to a model of the malocclusion and the transfer registration mold containing the brackets can thus be carried directly into the patient's mouth. In accordance with the present invention, however, the brackets are initially attached to a model the teeth of which are set in an ideal occlusion; thus, the transfer registration mold will not fit over the patient's malpositioned teeth. The orthodontist thus has two options at this point. One choice is to separate each individual tooth mold and its accompanying bracket from the overall registration and to use the individual mold as a guide means for accurately locating each bracket individually directly within the patient's mouth during the cementation process. Alternatively, the individually separated tooth-bracket registrations may be reassembled upon a model of the malocclusion, that is, a mold of the teeth in their original, uncorrected relationship. A unitizing second transfer registration mold is then made which may be used directly within the patient's mouth in order to facilitate the simultaneous positioning and cementing of multiple brackets upon the patient's teeth. Such a second transfer registration mold thus facilitates the positioning and cementing of brackets for an entire arch, if and when such simultaneity is desired.

The above-described method for constructing and positioning an orthodontic appliance utilizes a template for unequivocally accomplishing a precise placement of orthodontic brackets upon human teeth. Simplified, accurate clinical treatment is accomplished because the bracket placement procedure compensates for all tip, torque and individual tooth thickness and intrabracket position requirements. All facets of the invention are based upon the ideal final teeth positions which have been predetermined, and thus treatment proceeds using flat arch wires without positional approximations and/or corrections, modifications or the like. As noted hereinabove, the template may be used to construct arch wires prior to the commencement of treatment or as the treatment advances; in either case, the patient's dentition takes on the same relationships with respect to the appliance as it did in the ideal laboratory model.

The method of the present invention thus provides accurate and convenient procedures for placing orthodontic brackets within the patient's mouth. The single or multiple registration technique eliminates freehand placement of the brackets within the patient's mouth, and the template technique eliminates freehand placement of the brackets upon the teeth of the cast. All arch wires may be constructed in advance because arch size, arch form and bracket positions have been ideally established, recorded and accurately transferred to the patient.

All steps of the method including the manipulation of models, the template, the attachment of the brackets to the ideal model, the transfer registration, the arch wire construction and the finisher can all be accomplished or constructed by auxiliary personnel. Preconstructed arch wires which do not require the usual adjustments, as previously described, can be quickly changed, rendering the treatment of most malocclusions easier, less time consuming and less expensive.

If an elastic or rubber finishing device is included in the treatment plan, it may be constructed in accordance with standard techniques directly over the ideal model with the brackets or replicas of the brackets affixed thereto. The template, naturally, is not in place upon the ideal model during the forming of the finishing appliance. Such elastic finishers are generally used to close band spaces or to effect other minor finishing tooth movements. Usually, an ideal arrangement of teeth is made in the laboratory from the original model of the malocclusion or a model of the case just prior to or following the debanding procedure. There are two major disadvantages associated with the present state-of-the-art of finisher construction and utilization. First, finishers notably lack a positive locking system. The typical finisher attempts to compensate for this disadvantage by incorporating therein locking means, e.g., wire clasps and reinforcing metal inserts. While, ideally, these means should positively seat the finisher in a position so as to effect the final tooth movement, reality and experience dictate otherwise. The finisher, more often than not, becomes dislodged from one or the other of the dental arches during periods of jaw relaxation, thus losing a significant amount of its effectiveness. In addition, since it is relatively easy to dislodge, the patient can displace it without removing it from the mouth. The present invention prevents the occurrence of such an inadvertent or casual displacement. Second, the usual method of finisher construction precludes the use of brackets for retention. The present invention, which idealizes bracket-tooth positions prior to beginning treatment, provides a major advantage in that steps in the procedure do not require duplication in order to obtain the advantages described below.

In accordance with the method disclosed, brackets previously fixed to the teeth in the mouth serve as positive locks for the finisher during the final treatment stages. This eliminates any need for the patient to exert any force during treatment which would tend to continually force the finisher back into place after it has become displaced when, for example, the muscles of mastication are relaxed.

The preceding examples can be repeated with similar success by substituting the generically or specifically described components and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for constructing an orthodontic appliance to be placed in a patient's mouth so as to effect desired tooth repositioning, comprising the steps of:
   (a) forming a model of a patient's malocclusion consisting of an impression of the patient's teeth only;
   (b) separating and respositioning individual teeth with respect to the each other and the opposing arch on said model of a patient's malocclusion to form an ideal model;
   (c) providing a template which conforms to the arch size and form of said ideal model, and moving said template into juxtaposition relative to said ideal model;
   (d) fixing orthodontic brackets to the teeth of said ideal model to form a base means in accordance with the positional characteristics of said template while being held in an ideal position by means of said template so that each bracket is ideally positioned upon each tooth of said model; and
   (e) transferring said brackets in conjunction with said base means and affixing said brackets to the teeth of said patient with all tip, torque and tooth thickness considerations compensated for on each tooth and each arch.

2. A method according to claim 1, wherein the transfer of said brackets from said ideal model to the teeth of said patient further comprises the steps of:

(a) forming a transfer registration mold about the brackets while said brackets are disposed upon said ideal model;

(b) removing said transfer registration mold with said brackets from said ideal model; and (c) separating individual transfer registration molds to enable transfer of each of said brackets, along with said base means, directly to the corresponding teeth within the patient's mouth.

3. A method according to claim 1, wherein the transfer of said brackets from said ideal model to the teeth of said patient further comprises the steps of:

(a) forming a transfer registration mold over said brackets disposed upon said ideal model;

(b) removing said transfer registration mold and brackets;

(c) separating said transfer registration mold into individual transfer molds for individual teeth;

(d) placing said individually separated transfer registration molds containing said brackets on a model of the patient's malocclusion;

(e) forming a second transfer registration mold over the individual molds and brackets while said brackets are disposed upon said model of the malocclusion; and (f) inserting said second transfer registration mold, with said brackets disposed therein, into the mouth of said patient so as to transfer and secure the ideal position of said brackets and said base means to the teeth of said patient.

4. A method according to claim 1, further comprising the steps of:

(a) forming a resilient finisher upon the ideal model containing said brackets or replicas thereof fixed to the teeth; and (b) inserting said finisher over said brackets affixed to the teeth in the patient's mouth so as to accomplish finishing tooth movements of said patient's teeth in accordance with the tooth and bracket positional relationships determined by the template in conjunction with said original ideal model.

5. In an orthodontic method for repositioning a malocclusion towards an ideal position in a patient's mouth which includes affixing orthodontic brackets to at least one maloccluded tooth, the improvement which comprises forming a model of a patient's malocclusion and repositioning the model to form an idealized model for use in a bracket-to-tooth bonding procedure, said procedure including the use of a transfer registration mold to transfer the brackets from said idealized model to said at least one tooth in order to obtain precision placement of brackets with said idealized model in the patient's mouth.

6. In an orthodontic method for repositioning a malocclusion to an ideal position in a patient's mouth which includes the use of a resilient finisher means to effect final tooth movement to said ideal position, the improvement which comprises:

(a) providing an ideal model of a patient's tooth having orthodontic brackets ideally positioned upon the tooth of said ideal model;

(b) forming said finisher means directly over the ideal model with the brackets or replicas of the brackets affixed thereto; and (c) employing orthodontic brackets secured to said patient's tooth as a means for securing said finisher in the mouth to activate final tooth movement in accordance with the tooth and bracket positional relationship determined by said ideal model, whereby said brackets serve as a positive lock for said finisher during the final treatment stages and eliminate any need for the patient to exert any force during treatment which would tend to continually force the finisher back into place after it has become displaced.

* * * * *